(12) United States Patent
Ko

(10) Patent No.: US 7,517,536 B2
(45) Date of Patent: Apr. 14, 2009

(54) ANTIMICROBIAL COMPOSITIONS AND WOUND DRESSINGS

(75) Inventor: Tse-Hao Ko, Taichung (TW)

(73) Assignee: Feng Chia University, Taichung (TW)

( * ) Notice: Subject to any disclaimer, the term of this patent is extended or adjusted under 35 U.S.C. 154(b) by 463 days.

(21) Appl. No.: 11/347,716

(22) Filed: Feb. 3, 2006

(65) Prior Publication Data

US 2007/0122461 A1 May 31, 2007

(30) Foreign Application Priority Data

Nov. 25, 2005 (TW) .............................. 94141437 A

(51) Int. Cl.
*A61F 13/00* (2006.01)
*A61F 13/02* (2006.01)
*A61L 15/00* (2006.01)
*A61L 15/16* (2006.01)

(52) U.S. Cl. .................. 424/443; 424/445; 424/447; 424/448

(58) Field of Classification Search ............... 424/443, 424/445, 447, 448
See application file for complete search history.

(56) References Cited

U.S. PATENT DOCUMENTS

| 2,934,066 A | 4/1960 | Stowasser |
| 3,800,792 A | 4/1974 | McKnight et al. |
| 3,830,908 A | 8/1974 | Klippel |
| 5,340,363 A | 8/1994 | Fabo |
| 5,782,788 A | 7/1998 | Widemire |
| 6,692,773 B2 | 2/2004 | Burrell et al. |
| 2004/0259728 A1 | 12/2004 | Ko |

FOREIGN PATENT DOCUMENTS

JP  10-099678  4/1998

OTHER PUBLICATIONS http://www.burnsurgery.org/Modules/silver/images/section7b/Mid_partial_thickness3copy.jpg, "Mid-Partial Thickness Burn", date not provided.
Oya, et al., "Preparation of Pitch-Based Antibacterial Activated Carbon Fiber," *Carbon*, vol. 31, No. 8, pp. 1243-1247 (1993).
Fu, et al., "Studies on the Mechanism of the Reaction of Activated Carbon Fibers With Oxidants," *Carbon*, vol. 32, No. 4, pp. 593-598 (1994).
Wang, et al., "Preparation and Characterization of Antibacterial Vicose-Based Activated Carbon Fiber Supporting Silver," *Carbon*, vol. 11, pp. 1567-1571 (1998).

*Primary Examiner*—Raymond J Henley, III
(74) *Attorney, Agent, or Firm*—Patterson, Thuente, Skaar & Christensen, P.A.

(57) ABSTRACT

The present invention relates to a wound dressing comprising a flexible base layer and an antimicrobial material, wherein the antimicrobial material comprises an activated carbon-carried noble metal, the activated carbon is selected from the group consisting of an activated carbon powder, an activated carbon particle, an activated carbon fiber, and a combination thereof, and the noble metal is selected from the group consisting of silver, gold, palladium, platinum, copper, zinc, and a combination thereof. The invention also relates to an antimicrobial composition for topical use on skin, in which the composition comprises the aforementioned activated carbon-carried noble metal.

10 Claims, 3 Drawing Sheets

ANTIMICROBIAL COMPOSITIONS AND WOUND DRESSINGS

FIELD OF THE INVENTION

The present invention relates to the use of an activated carbon-carried noble metal in an antimicrobial composition and an antimicrobial wound dressing. In particular, the present invention actively aggregates and destroys the microbes close to said composition and wound dressing to prevent microbial infection.

BACKGROUND OF THE INVENTION

In the past, antimicrobial drugs have been directly applied onto the injured part of the body. Recently, depending on the type of wound, medical wound dressings, such as medical tape, patch, gelatin film bandage and band-aids, have been adopted to cover the wound, thereby, isolating the wound from improper contact with the external atmosphere, protecting the wound, preventing infection, and reducing pain.

It is known that the use of noble metals such as silver, gold, palladium, platinum, copper, and zinc in dressings, have effectively killed microbes. The use of such noble metals in dressings has been disclosed in many references. For example, Robert Edward Burrell et al. (U.S. Pat. No. 6,692,773 B2) disclose the use of a noble metal such as silver, gold, palladium, or platinum, or an alloy or a compound thereof, in a nanocrystalline form with a grain size of less than 100 nm, in coating a fabric to provide a dressing having the antiproliferative effect. Widemire (U.S. Pat. No. 5,782,788) discloses the fixation of a silver foil layer on a gauze pad to inhibit the growth of bacteria, virus, and fungus. Fabo (U.S. Pat. No. 5,340,363) discloses a dressing comprising an outer absorbent layer and an inner porous hydrophobic layer knitted of elastic threads and encapsulated by a soft hydrophobic silicone or polyurethane gel, wherein the gel can be used as a carrier for an antibacterial agent (e.g., zinc), a pain-relieving substance, and an agent that stimulates wound repair. Klippel et al. (U.S. Pat. No. 3,830,908) disclose the use of micronized allantoin as a carrier for a bactericidal or bacteriostatic ingredient (such as silver citro allantoinate). The composition is dispersed on the surface of a plastic air splint or other bandaging product to provide antibacterial action, depending on the molecular dissociation. McKnight et al. (U.S. Pat. No. 3,800,792) disclose a surgical dressing comprising a layer of tanned and reconstituted collagen foam film, which is laminated to a thick continuous layer of an inert polymer. The collagen layer contains a finely-divided silver metal added by soaking the collagen film in Tollen's reagent. Stowasser (U.S. Pat. No. 2,934,066) discloses a dressing of absorbent metal-coated fibers, such as a carding fleece coated with aluminum and backed by compressed cellulose, and polyamide fibers coated with vacuum-deposited silver.

Given the prior technology mentioned above, it is clear that antimicrobial noble metals are widely used in therapy, especially in dressing. However, the use of these noble metals still focuses on the noble metal alone and at most, the noble metal in a form of an alloy or compound. Although such use can provide an antimicrobial effect, the microbes are only destroyed upon "coincidentally" contact with the noble metal. Because of this, the noble metals merely provide a "passive" antimicrobial effect.

Moreover, as known by persons having ordinary skill in the art, the above-mentioned noble metals can only fight microbes in the presence of moisture. Therefore, for practical use, the medium must always be moist. If necessary, water is added to provide a moist environment. For example, according to U.S. Pat. No. 6,692,773 B2, when a nanocrystalline noble metal is coated onto a dressing for topical use on skin, the dressing must maintain a moist condition for the noble metal to exhibit the desired efficacy (see column 6,line 64 to column 7,line 17). Consequently, U.S. Pat. No. 6,692,773 B2 further discloses the preference for an absorbent layer in the dressing to hold in moisture for activating the noble metal (see said patent, column 5,lines 33 to 37). Such need of moisture for activating noble metals can also can be found in other references, such as the content published via the website, http://www.burnsurgery.org/Modules/silver/images/section-7b/Mid_partial_thickness3copy.jpg.

The present invention relates to an improvement of the therapeutic application of a noble metal that has an antimicrobial effect. The present invention actively aggregates and then destroys microbes so as to effectively reduce, and even prevent, the microbial infection.

SUMMARY OF THE INVENTION

The present invention aims to provide a method for preventing a wound from a microbial infection comprising covering the wound with a noble metal-carrying activated carbon fiber cloth. The noble metal is selected from the group consisting of silver, gold, palladium, platinum, copper, zinc, and a combination thereof.

The present invention also aims to provide a wound dressing comprising a flexible base layer and an antimicrobial material, wherein the antimicrobial material comprises an activated carbon-carried noble metal, the activated carbon is selected from the group consisting of an activated carbon powder, an activated carbon particle, an activated carbon fiber, and a combination thereof, and the noble metal is selected from the group consisting of silver, gold, palladium, platinum, copper, zinc, and a combination thereof. In addition, this dressing can optionally comprise a pressure sensitive adhesive component and other therapeutically active components. Those components can be either incorporated into the antimicrobial material or exist individually in a separate layer.

The present invention further aims to provide an antimicrobial composition for topical use on skin comprising an activated carbon-carried noble metal, wherein the activated carbon is selected from the group consisting of an activated carbon powder, an activated carbon particle, an activated carbon fiber, and a combination thereof, and the noble metal is selected from the group consisting of silver, gold, palladium, platinum, copper, zinc, and a combination thereof. Said composition can optionally comprise other therapeutically active components.

It is believed that the activated carbon can aggregate and absorb microbes on its surface due to the electrostatic interactions or van der Waal forces between the microbes and the surface of the activated carbon, as well as the bioaffinity of the activated carbon. Consequently, as compared with the passive effect of the prior art in which microbes are destroyed and killed when "coincidentally" in contact with the noble metal, the present invention adopts an active manner in aggregating and destroying the microbes around the noble metal, providing a superior antimicrobial effect. Moreover, the composition and wound dressing of the present invention activate the used noble metal without the need for adding moisture or utilizing other approaches. As compared with the prior art that requires moisture and/or a moisture-holding component such as an absorbent layer to activate the antimicrobial noble metal, the present invention provides a simpler way to attain the desired antimicrobial benefit.

Figure 1:
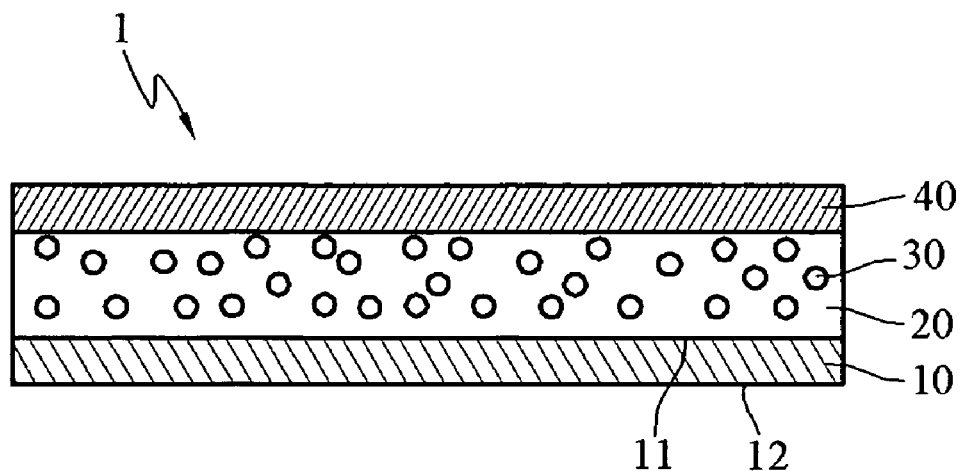
FIG. 1 shows a schematic diagram of an embodiment of the wound dressing of the present invention, wherein the wound dressing is a patch.

| | |
|---|---|
| 1 | patch |
| 10 | base layer |
| 11, 12 | first surface and second surface of the base layer 10 |
| 20 | antimicrobial layer |
| 30 | noble metal-carrying activated carbon |
| 40 | protective layer |
| 50 | drug layer |
| 100 | gauze |
| 110 | base layer |
| 111, 112 | first surface and second surface of the base layer 110 |
| 120 | antimicrobial coating |
| 200 | band-aid |
| 210 | base layer |
| 211, 212 | first surface and second surface of the base layer 210 |
| 220 | pressure sensitive adhesive layer |
| 230 | antimicrobial fabric layer |
| 240 | protective layer |

DESCRIPTION OF THE INVENTION

The wound dressing of the present invention comprises a flexible base layer and an antimicrobial material, wherein the flexible base layer comprises a first surface and a second surface and the antimicrobial material is applied on at least one portion of said first surface and contains an activated carbon-carried noble metal.

The flexible base layer contained in the wound dressing of the present invention can be porous or drug-impermeable. If a gauze or band-aid is desired, the flexible base is suitably composed of a porous material, preferably of a non-adhesive material. If a patch is desired, it is suitable to adopt a drug-impermeable base in the present invention. Materials that are conventionally used for providing a base for a wound dressing and meet the above porous or drug-impermeable requirement can be used in the present invention. For example, the porous base can be prepared from a woven fabric or non-woven fabric, preferably non-woven fabric, composed of one or more the following materials: natural fiber, polyolefin fiber, polyester fiber, polyurethane fiber, polyamide fiber, polycellulose fiber, and cotton fiber. Polymers suitable for providing a drug-impermeable base comprise polyvinyl chloride, polyvinyl dichloride, polyolefin (e.g., ethylene vinylacetate copolymer, polyethylene, and polypropylene), polyurea, and polyester (e.g., polyethylene terephthlate). The drug-impermeable base can be a single polymer layer or film, or a laminate composed of multiple polymer layers.

The noble metal-carrying activated carbon contained in the antimicrobial material of the wound dressing of the present invention is selected from the group consisting of an activated carbon powder, an activated carbon particle, an activated carbon fiber, and a combination thereof, and an activated carbon fiber is preferred. The noble metal is selected from the group consisting of silver, gold, palladium, platinum, copper, zinc, and a combination thereof, and silver is preferred.

Any means known prior to the filing of the subject application, such as thermocracking, electroplating, electroless plating, or vacuum plating, can be used to carry the noble metal on the activated carbon powder, activated carbon particle, or activated carbon fiber. Moreover, the noble metal can be carried on activated carbon in any known forms. To effectively release the noble metal ion that has antimicrobial activity, it is preferred that the noble metal particulate carried on activated carbon is of a size of nanometer, wherein the maximum grain size of the particulate is about 100 nm, preferably no more than 50 nm, and most preferably no more than 25 nm.

For example, a process which can be used for preparing a silver-carrying activated carbon fiber useful in the present invention comprises the following steps:

a. Immersing in a Solution of Silver Nitrate

An activated carbon fiber is immersed in a solution of silver nitrate for 1 to 720 minutes to reduce the silver on the surface of the activated carbon fiber, followed by a drying step to remove the water phase. The pH of the silver nitrate solution is maintained between the range of 3 and 8. The drying step is conducted at a temperature ranges from 25° C. to 150° C.

b. High Temperature Thermocracking

The silver-containing activated carbon fiber is placed in a high temperature furnace, with a controlled temperature between 120° C. and 450° C. for 5 to 120 minutes, to break the silver on the surface of the activated carbon fiber into ultra fine metal particles. To avoid the oxidization or podzolization of the activated carbon fiber, it is preferred to conduct the high temperature thermocracking in vacuum or in the presence of a protective air such as nitrogen.

c. Washing

The high-temperature thermocracked silver-containing activated carbon fiber is washed with water for 1 minute to 600 hours to remove the excess silver on the surface of the activated carbon fiber. This step is followed by baking the washed, activated carbon fiber to produce a silver-carrying activated carbon fiber.

The silver-carrying activated carbon fiber prepared according to the above process has a BET specific surface of above 400 m/g, carbon content of above 50 wt %, silver content of above 0.001 wt %, and a density of above 1.8 g/m$^3$. A fiber selected from the group consisting of polypropylene nitrile fiber, cellulose fiber, bitumen fiber, phenolic fiber, and a combination thereof can be used in the above process to prepare an antimicrobial noble metal-carrying activated carbon fiber which has the above properties. The noble metal-carrying activated carbon fiber for use in the wound dressing of the present invention can be in the form of fiber, cloth, carpet, band, or yarn.

If the noble metal-carrying activated carbon fiber is produced as a noble metal-carrying activated carbon fiber cloth, it can be directly applied to cover a wound to prevent the wound from the infection of microbes. In this case, the cloth can be fixed by any approaches well known in the art. For instance, a bandage can be used to fix the noble metal-carrying activated carbon fiber cloth to cover the wound and prevent it from the microbial infection. Optionally, a therapeutically active component can be coated on at least one portion of a surface of the cloth. The therapeutically active component is selected from the group consisting of acrisorcin, haloprogin, iodochlorhydroxyquin, tolnaftate, triacetin, centella asiatica, econazole nitrate, mafenide, mupirocin, povidone iodine, and a mixture thereof.

The relevant details of the above preparation process can be found in the co-pending U.S. Ser. No. 10/866,655,which was also assigned to this assignee and corresponding to Taiwan (ROC) Patent Publication No. 0059115.Moreover, the preparation of a silver-carrying activated carbon fiber can be found in JP 10-99678;T. A. Oya, T. Wakahara, and S. Yoshida, Carbon, 31, 1243-1247, 1993;Fu, R., H. Zeng, and Y. Lu, "Studies on the Mechanisms of the Reaction of Activated Carbon Fibers with Oxidants," *Carbon,* 32(4), 593-598 (1994); and Wang, Y. L., Y. Z. Wan, X. H. Dong, G. X. Cheng, H. M. Tao, and T. Y Wen, "Preparation and Characterization of Antibacterial Viscose-based Activated Carbon Fiber Supporting Silver," *Carbon,* 36(11), 1567-1571(1998). The above documents are incorporated hereinto for reference.

If the base layer of the wound dressing is a porous base, the antimicrobial material can be continuously or discontinuously coated on at least one portion of the first surface of the base. Optionally, the antimicrobial material further comprises an adhesive component to enhance its bond with the base. Therefore, if the antimicrobial material will come into contact with the wound or the surrounding skin, an adhesive that does not stimulate the skin, preferably a pressure sensitive adhesive, is more suitable. If a noble metal-carrying activated carbon fiber is used as the antimicrobial material, the activated carbon fiber can be incorporated into the base fiber to provide a wound dressing of the present invention. For example, the activated carbon fiber is incorporated by a co-weaving manner to provide a porous base in a form of woven fabric. Moreover, if the noble metal-carrying activated carbon contained in the antimicrobial material is an activated carbon fiber fabric, such as cloth, the antimicrobial material can be applied upon at least one portion of the first surface of the base as a fabric layer. The activated carbon fiber fabric and the base can be combined by way of such as ultrasonic welding to laminate the antimicrobial material fabric layer and the base, or utilizing an additional adhesive layer to bind the two layers. As a result, a wound dressing in the form of a band-aid is provided.

If the base layer of the wound dressing is drug-impermeable, the antimicrobial material can be directly applied on at least one portion of the first surface of the base as a single material layer. In this respect, if the noble metal-carrying activated carbon contained in the antimicrobial material is an activated carbon fiber, the antimicrobial material containing said activated carbon fiber can be applied on at least one portion of the first surface of the base as a fabric layer. The fabric layer can be laminated to the base layer by utilizing methods such as ultrasonic welding. In this case, the antimicrobial material fabric layer is composed of noble metal-carrying activated carbon fiber and natural or synthetic fiber, or is an activated carbon fiber fabric. Optionally, an additional adhesive layer can be used on the first surface of the base to bind the antimicrobial material layer and the first surface. Alternatively, the antimicrobial material layer can directly contain an adhesive. In this case, if the antimicrobial material layer will come into contact with the wound or the surrounding skin, an adhesive that does not stimulate the skin, preferably a pressure sensitive adhesive, is more suitable.

Adhesives that are known to be commonly applied in wound dressings can be utilized in the present invention. It is preferred to use a pressure sensitive adhesive, e.g., those disclosed in U.S. Pat. Nos. 4,675,009, 4,696,854, 5,536,263, 5,741,510, 5,972,377, and 6,495,158 B1.The above patents are incorporated hereinto for reference. For example, the pressure sensitive adhesives useful in the present invention include, but not limited to, the following pressure sensitive adhesives for use in a percutaneous patch: polyacrylate, siloxane, or polyisobutadiene.

The wound dressing of the present invention can optionally comprise other therapeutically active components to provide additional therapeutic benefits. As indicated above, the therapeutically active component can either be directly incorporated into the antimicrobial material, or exist individually, for example, in a separate layer. If the therapeutically active component and the antimicrobial material individually exist in separate drug layers, the antimicrobial material may be placed between the base layer and the drug layer as a single layer. As mentioned above, the antimicrobial material can also be applied on the porous base as a coating. The drug layer can further comprise a pressure sensitive adhesive component suitable for percutaneous patch. Alternatively, the antimicrobial material layer can be inserted in between two drug layers (i.e., base layer, drug layer, antimicrobial material layer, and drug layer in order). The therapeutically active components and pressure sensitive adhesive components contained in the drug layers can be the same or different.

Any therapeutically active component for healing skin wounds can be applied in the wound dressing of the present invention. For example, the therapeutically active component useful in the wound dressing of the present invention comprises, but is not limited to, an antifungal agent such as erythromycin, tetracycline, clindamycin, cephalosporin, acrisorcin, haloprogin, iodochlorhydroxyquin, tolnaftate, and triacetin, as well as a drug component for trauma, burn, and scald such as centella asiatica, econazole nitrate, mafenide, mupirocin, and povidone iodine.

Optionally, the wound dressing of the present invention can further comprise a protective layer on the exterior surface of the material layer which contains a pressure sensitive adhesive (the material layer can be a drug layer or an antimicrobial material layer) to protect the material. The protective layer can be a single material layer or two material layers which partially overlap each other. Any known protective layers useful in wound dressings can be used in the present invention. For example, a film consisted of one or more the following materials can be used as the protective layer: polyurethane, nylon, polyamide, polycellulose, polyvinyl chloride, polyvinyl dichloride, polyolefin (e.g., ethylene vinylacetate copolymer, polyethylene, and polypropylene), polyurea, and polyester (e.g., polyethylene terephthlate).

The known technology used in the wound dressing of the present invention is briefly mentioned to facilitate the explication of the present invention. The technical features and contents of the present invention will be further explained according to the drawings. Nonetheless, the relevant drawings are not drawn according to the actual proportion, since they function to express the features of the present invention only.

FIG. 1 shows a side view of an embodiment of the wound dressing of the present invention, wherein the wound dressing is a patch (1) for healing a wound. The patch (1) contains a base layer (10) having a first surface (11) and a second surface (12), an antimicrobial layer (20) on said first surface, and a protective layer (40) on said antimicrobial layer (20). The antimicrobial layer (20) comprises a pressure sensitive adhesive (not depicted) and a silver-carrying activated carbon (30), and, optionally, a therapeutically active component (not depicted) for healing trauma, burn, or scald wounds. The activated carbon can be an activated carbon powder, an activated carbon particle, an activated carbon fiber, or a combination thereof. When using the patch (1), the protective layer

(40) is torn from said antimicrobial layer (20) and then the patch (1) is stuck on to the wound or injured part of the body with the side containing the antimicrobial layer (20).

Figure 2:
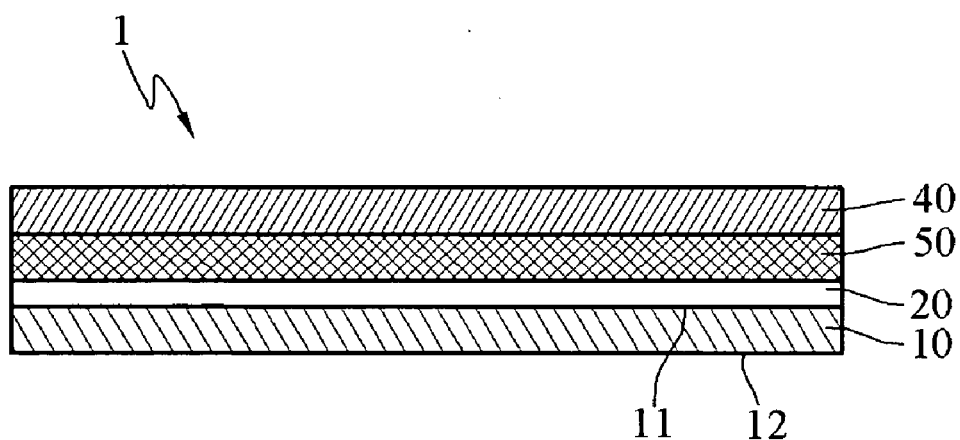
FIG. 2 shows a schematic diagram of another embodiment of the wound dressing of the present invention, wherein the wound dressing is a patch.

FIG. 2 shows a side view of another embodiment of the wound dressing of the present invention. The schematic patch (1) contains a base layer (10) having a first surface (11) and a second surface (12), an antimicrobial layer (20) on said first surface (11), a drug layer (50) coated on said antimicrobial layer (20), and a protective layer (40) on said drug layer (50). The drug layer (50) contains a therapeutically active component (not depicted) for healing burn and scald wounds and a pressure sensitive adhesive (not depicted). The antimicrobial layer (20) is composed of a silver-carrying activated carbon fiber fabric. When using the patch (1), the protective layer (40) is torn from said drug layer (50) and then the patch (1) is stuck on to the wound or injured part of the body with the side containing the drug layer (50). Optionally, another drug layer is placed between the base layer (10) and the antimicrobial layer (20).

Figure 3:
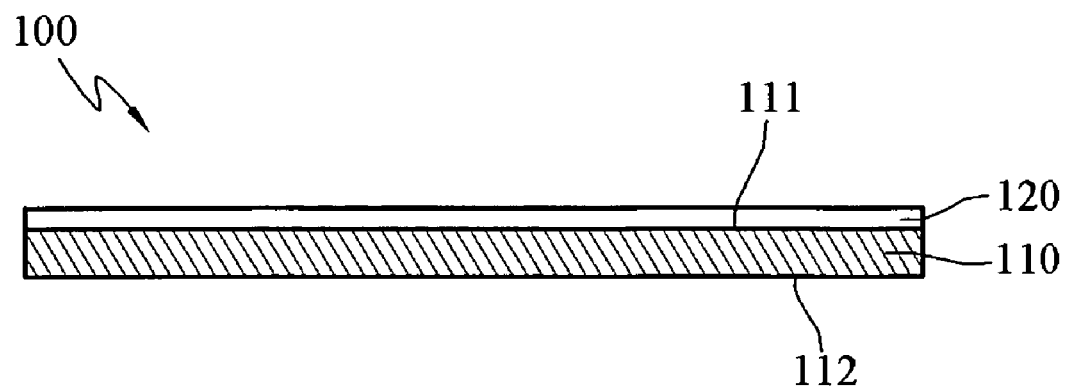
FIG. 3 shows a schematic diagram of a further embodiment of the wound dressing of the present invention, wherein the wound dressing is gauze.
Figure 3A:
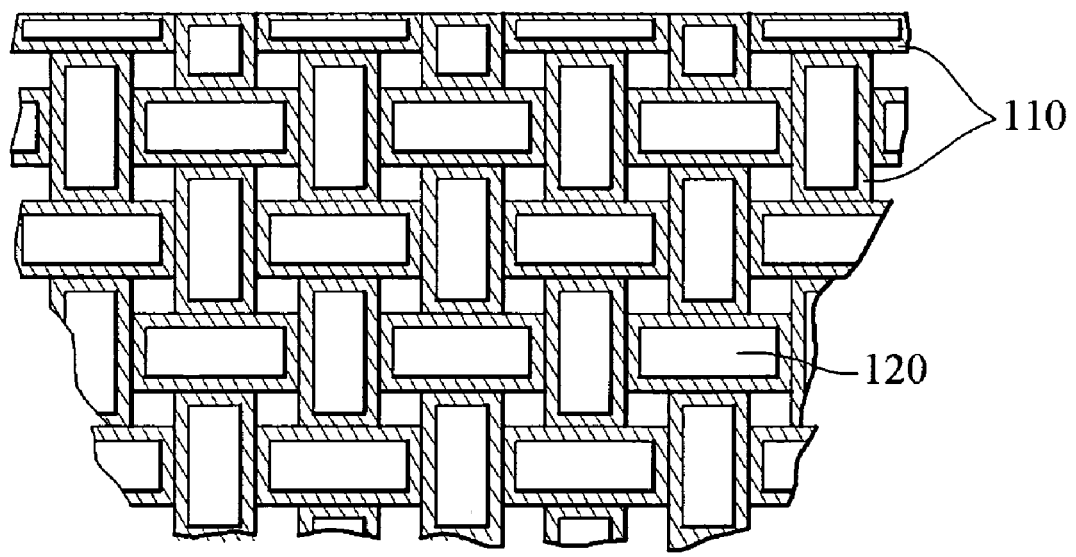

FIG. 3 shows a side view of another embodiment of the wound dressing of the present invention, wherein the wound dressing is a gauze (100). FIG. 3A is a partially enlarged front view of the gauze (100). As depicted in FIGS. 3 and 3A, the gauze (100) contains a fiber fabric base layer (110) that has a first surface (111), a second surface (112) and an antimicrobial coating (120) applied on at least one portion of said first surface (111). The antimicrobial coating (120) contains a silver-carrying activated carbon (not depicted) and a pressure sensitive adhesive (not depicted).

Figure 4:
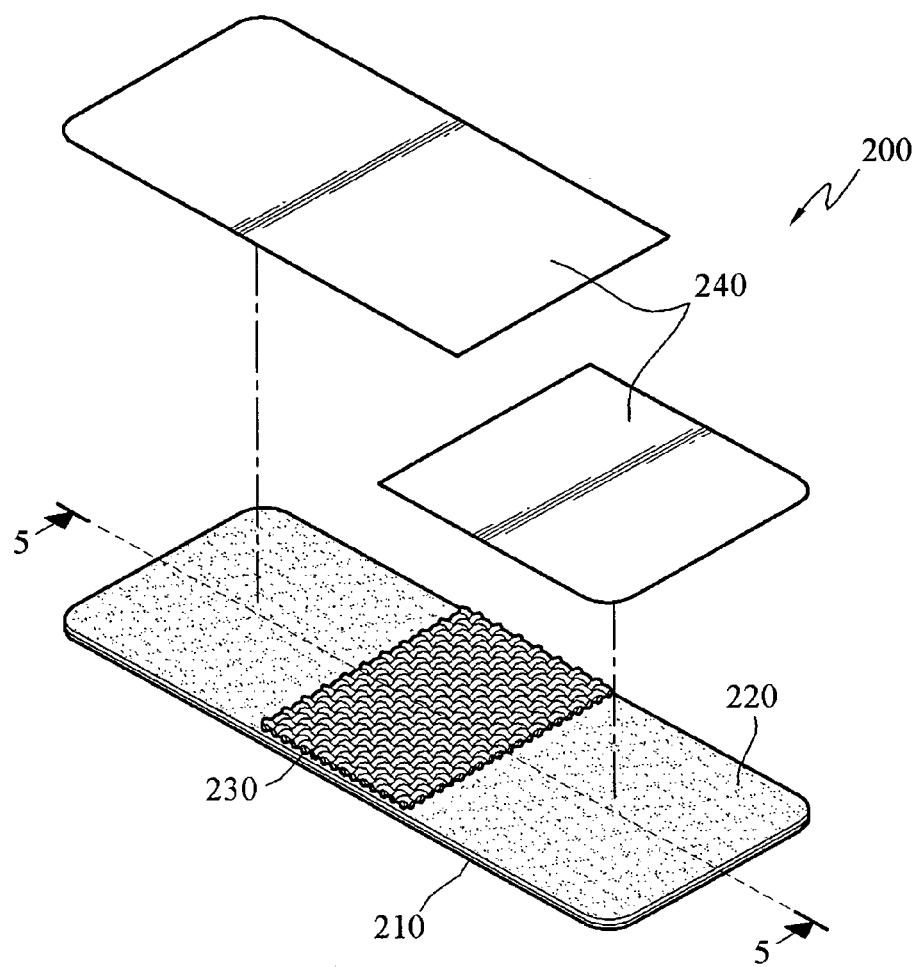
FIG. 4 shows a schematic diagram of another further embodiment of the wound dressing of the present invention, wherein the wound dressing is a band-aid.
Figure 5:
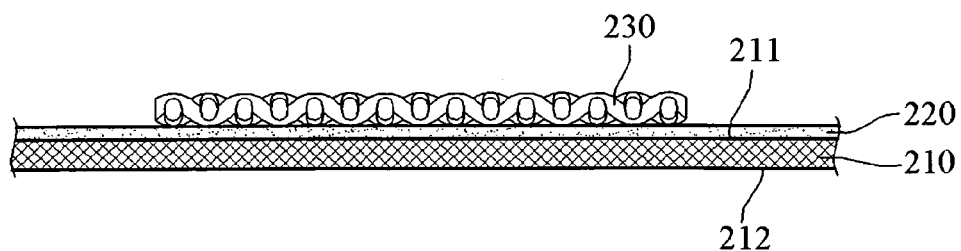
FIG. 5 shows a cross-section view along line 5-5 in FIG. 4.

FIG. 4 shows a schematic diagram of another embodiment of the wound dressing of the present invention, wherein the wound dressing is a band-aid (200). FIG. 5 shows a cross-section view along line 5-5 of FIG. 4. As depicted in FIGS. 4 and 5, the band-aid (200) contains a base layer (210) that has a first surface (211), a second surface (212), a pressure sensitive adhesive (220) coated on said first surface(211), an antimicrobial fabric layer (230) preferably positioned on the center of the base layer (21), and two protective layers (240) which partially overlap each other. The antimicrobial fabric layer (230) is a gauze layer comprising a silver-carrying activated carbon fiber. Optionally, a drug layer (not depicted) containing another drug component for healing trauma, burn, or scald wounds can be applied on the gauze layer to provide additional therapeutic effects.

In the wound dressing of the present invention where the noble metal is carried on the activated carbon, the activated carbon takes the initiative to absorb and aggregate the microbes close to the wound dressing on its surface. The activated carbon-carried noble metal proceeds to destroy the absorbed/aggregated microbes to provide an aseptic condition for the wound, promote the wound occlusion, and reduce the scar. Moreover, because the activated carbon absorbs moisture (normally 5 to 20 wt %), the moisture can activate the noble metal carried thereon. Therefore, it is unnecessary to further add moisture or adopt other manners to activate the noble metal. By utilizing a simpler manner, the present invention attains the desired antimicrobial benefit.

The present invention further provides an antimicrobial composition for topical use on skin comprising an activated carbon-carried noble metal. The activated carbon is selected from the group consisting of an activated carbon powder, an activated carbon particle, an activated carbon fiber, or a combination thereof. The noble metal is selected from the group consisting of silver, gold, palladium, platinum, copper, zinc, or a combination thereof. Preferably, the activated carbon-carried noble metal is activated carbon fiber-carried silver.

In the composition of the present invention, the amount of the activated carbon-carried noble metal, in view of the weight of the noble metal per se, is typically about 0.001 to about 30 wt %, preferably about 0.01 to 10 wt %. It is preferred that the noble metal is carried on an activated carbon fiber in the particulate form. To more effectively release the noble metal ions that have the antimicrobial activity, it is more preferred that the activated carbon fiber-carried particulate noble metal is in the nanometer particulate form, and has a maximum size of about 100 nm. More preferably, the maximum size is no more than 50 nm, and most preferably no more than 25 nm.

Optionally, the composition of the present invention further contains a therapeutically active component in a therapeutically effective amount. For example, the therapeutically active components comprise, but not limited to, an antimicrobial agent, an antifungal agent, or other therapeutic components for trauma, burn, or scald wounds. For example, the composition of the present invention can optionally contain erythromycin, tetracycline, clindamycion, cephalosporin, triclosan, phenoxy isopropanol, chlorhexidine gludonate, povidone iodine, acrisorcin, haloprogin, iodochlorhydroxyquin, tolnaftate, triacetin, centella asiatica, econazole nitrate, mafenide, mupirocin, or povidone iodine.

In addition to the active components, the composition of the present invention can further contain a non-toxic, pharmaceutically and skin acceptable carrier, diluent, and excipient suitable for topical use. The carrier, diluent, and excipient, and the standard doses of known pharmacological agents can be found in U.S. Pat. No. 6,692,773 B2. The contents are incorporated hereinto for reference.

The composition for topical use of the present invention can be in various dosage forms, such as a gel, a paste, an ointment, a cream, an emulsion, and a suspension. The noble metal-carrying activated carbon can be mixed with the pharmaceutically acceptable carrier, diluent, or excipient and other optional active components under aseptic conditions to provide the desired dosage form. For example, a suitable thickener or gelling agent is added to an aqueous or oil base to formulate an ointment or cream. Water can be used as the aqueous base. Depending upon the inherent properties of the base, aluminum stearate and hydrogenated lanolin can be used as a thickener. Starch, tragacanth, cellulose derivative, polyethylene glycol, silicones, bentonite, silicic acid, talc, or a mixture thereof can be used as the excipient to provide the composition of the present invention in a dosage form of a paste, an ointment, a cream, or a gel.

It should be noted that the major difference between the subject invention and the prior art lies in that the noble metal, that has the antimicrobial characteristic, is used in the present invention in the form of an activated carbon-carried noble metal. Because the activated carbon contains moisture, the present invention can activate the noble metal to provide the antimicrobial benefit without adding moisture. Moreover, since the activated carbon can aggregate microbes, the present invention improves the "passive" benefit attained by the prior art, in which the noble metal merely kills the microbes upon contact. The present invention takes an active manner to destroy the microbes. Therefore, the present invention is suitable in situations known in the prior art where the noble metals are topically used on skins to destroy microbes and inhibit their growth, so as to provide a superior antimicrobial benefit.

Although the present invention has been disclosed above, the disclosure does not limit the present invention. Persons having ordinary skill in the art can make any changes or modifications without departing from the spirit and scope of the present invention. Consequently, the scope of protection of the present invention is based on the claims attached.

The invention claimed is:

1. A wound dressing, comprising a flexible base layer having a first surface and a second surface and an antimicrobial material, wherein said antimicrobial material comprises an activated carbon-carried noble metal, said activated carbon is selected from the group consisting of an activated carbon powder, an activated carbon particle, an activated carbon fiber, and a combination thereof, and said noble metal is selected from the group consisting of silver, gold, palladium, platinum, copper, zinc, and a combination thereof.

2. The dressing according to claim 1, wherein said activated carbon is a carbon active fiber and said noble metal is silver.

3. The dressing according to claim 2, wherein said noble metal is in a form of particulate and has a maximum grain size of no more than 100 nm.

4. The dressing according to claim 1, wherein said flexible base layer is porous and said antimicrobial material is continuously or discontinuously coated on at least one portion of said first surface.

5. The dressing according to claim 1, wherein said antimicrobial material is a material layer or a fabric layer and covers on at least one portion of said first surface.

6. The dressing according to claim 5, further comprising an adhesive layer, wherein said antimicrobial material is a fabric layer and said adhesive layer is placed between said antimicrobial material fabric layer and said first surface.

7. The dressing according to claim 1, further comprising a therapeutically active component, wherein said therapeutically active component is selected from the group consisting of acrisorcin, haloprogin, iodochlorhydroxyquin, tolnaflate, triacetin, centella asiatica, econazole nitrate, mafenide, mupirocin, povidone iodine, and a mixture thereof.

8. The dressing according to claim 7, wherein said therapeutically active component is incorporated into said antimicrobial material and said antimicrobial material further comprises a pressure sensitive adhesive component.

9. The dressing according to claim 7, wherein said therapeutically active exists in a material layer and said antimicrobial material is placed between said material layer and said first surface.

10. The dressing according to claim 9, wherein said material layer further comprises a first pressure sensitive adhesive component and/or said antimicrobial material further comprises a second pressure sensitive adhesive component, and the first pressure sensitive adhesive component and the second pressure sensitive adhesive component are the same or different.

* * * * *